United States Patent [19]

Darms et al.

[11] 4,306,073
[45] Dec. 15, 1981

[54] SILICON-MODIFIED BIS-PHTHALIC ACID DERIVATIVES

[75] Inventors: Roland Darms, Therwil; Siegfried Wyler, Dornach, both of Switzerland; Gerd Greber, Bad Vöslau, Austria

[73] Assignee: Ciba-Geigy Corporation, Ardsley, N.Y.

[21] Appl. No.: 114,471

[22] Filed: Jan. 23, 1980

Related U.S. Application Data

[63] Continuation of Ser. No. 938,170, Aug. 30, 1978, abandoned.

[30] Foreign Application Priority Data

Sep. 9, 1977 [CH] Switzerland .................. 11067/77

[51] Int. Cl.³ .................................. C07F 7/10
[52] U.S. Cl. ........................... 556/419; 260/313.1; 260/325 R; 260/326 R; 260/326.13 R; 260/333; 260/346.11; 260/347.3; 546/14; 549/4
[58] Field of Search .................................. 556/419

[56] References Cited

U.S. PATENT DOCUMENTS

| | | | |
|---|---|---|---|
| 3,325,450 | 6/1967 | Holub | 556/419 X |
| 4,051,163 | 9/1977 | Berger | 556/419 |
| 4,088,670 | 5/1978 | Bargain et al. | 556/419 X |
| 4,200,724 | 4/1980 | Darms et al. | 556/419 X |
| 4,213,914 | 7/1980 | Bargain et al. | 556/419 |

FOREIGN PATENT DOCUMENTS 2543883 4/1976 Fed. Rep. of Germany ...... 556/419

Primary Examiner—Paul F. Shaver
Attorney, Agent, or Firm—Harry Falber

[57] ABSTRACT

The Si-modified bis-phthalic acid derivatives according to the invention are monomeric, oligomeric or polymeric compounds. An example of a monomeric compound of the invention is the amidoacid of the formula

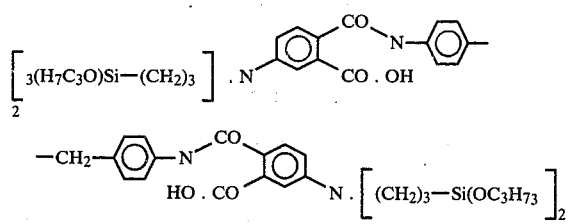

which is formed by reacting 4,4'-diaminodiphenylmethane and 4-N,N'-bis-[3-tri-n-propoxy)-silyl-propyl]-aminophthalic anhydride in solution, in a molar ratio of 1:2. To produce oligomeric or polymeric compounds, the reaction has to be carried out with a 3rd component, for example pyromellitic dianhydride.

The products are used as adhesion promoters, for example between inorganic solids and organic resins.

9 Claims, No Drawings

SILICON-MODIFIED BIS-PHTHALIC ACID DERIVATIVES

This is a continuation of application Ser. No. 938,170 filed on Aug. 30, 1978, now abandoned.

The present invention relates to new silicon-modified bis-phthalic acid derivatives, a process for their preparation and their use as adhesion promoters, for example between inorganic solids and organic resins.

The literature discloses that various silanes, for example vinyltrichlorosilane, vinyl-tris-(2-methoxyethoxy)-silane and γ-aminopropyltriethoxysilane can be used as adhesion promoters for various applications, for example for the manufacture of glass fibre-reinforced plastics, and for sealants, lacquers and adhesives [compare, for example, Defazet, 28, 207–211 (1974) and Kunststoffe, 55, 909–912 (1965)]. The properties of the products obtained with these known adhesion promoters, however, in part leave something to be desired, especially in respect of water absorption, resistance to thermal oxidation, and/or electrical properties.

It is the object of the invention to provide novel adhesion promoters, with which the above disadvantages can be overcome.

The novel silicon-modified bis-phthalic acid derivatives correspond to the formula I

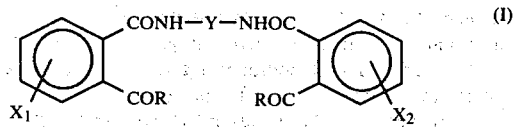

in which $X_1$ and $X_2$ independently of one another are a group

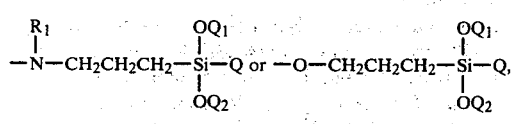

the two R independently of one another are —OH, alkoxy with 1–12 C atoms or phenoxy, $R_1$ is alkyl with 2–7 C atoms, cycloalkyl with 5–7 C atoms, benzyl or

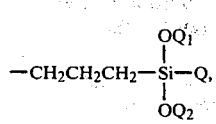

Q is methyl, phenyl or —OQ$_3$, Q$_1$, Q$_2$ and Q$_3$ independently of one another are alkyl with 1–6 C atoms or phenyl and Y is a structural element of the formula II

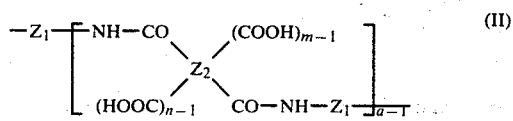

in which a is an integer from 1 to 15, the individual indices m and n independently of one another are 1 or 2, the individual radicals $Z_1$ independently of one another are an aliphatic radical with at least 2 C atoms, or a cycloaliphatic, araliphatic, carbocyclic-aromatic or heterocyclic-aromatic radical and the individual radicals $Z_2$ independently of one another are an aliphatic radical with at least 2 C atoms, or a cycloaliphatic, carbocylic-aromatic or heterocyclic-aromatic radical, in which the carboxamide and carboxyl groups are bonded to different C atoms, and carboxyl groups bonded to cyclic radicals $Z_2$ are each in the ortho-position to a carboxamide group.

The invention also relates to the corresponding cyclised imide derivatives.

The compounds of the formula I may be monomeric, polymeric or oligomeric.

The compounds of the formula I and the corresponding cyclised imide derivatives can be prepared by a method wherein a compound of the formula III

or a mixture of two different compounds of the formula III, in which $R_2$ and $R_3$ independently of one another are —OH, alkoxy with 1–12 C atoms or phenoxy or $R_2$ and $R_3$ together are the —O—group and X is a group corresponding to $X_1$ or $X_2$, is reacted in essentially stoichiometric amount with a compound of the formula IV $$H_2N-Y-NH_2 \qquad (IV)$$

in which Y is as defined under formula I or II, after which the reaction product obtained may be may not be cyclised to the imide.

Alkoxy groups R, $R_2$ and $R_3$ and alkyl groups $R_1$, $Q_1$, $Q_2$ and $Q_3$ may be straight-chain or branched. Examples of alkoxy and alkyl groups according to the definition are, respectively, the methoxy, ethoxy, n-propoxy, isopropoxy, n-butoxy, n-hexyloxy, n-decyloxy and n-dodecyloxy group, and the methyl, ethyl, n-propyl, isopropyl, n-butyl, tert.-butyl, n-pentyl, n-hexyl and n-heptyl group.

R, $R_2$ and $R_3$ are preferably —OH or alkoxy with 1–4 C atoms, especially methoxy or ethoxy. In a very particularly preferred embodiment, $R_2$ and $R_3$ together, however, form the group —O—and R is —OH.

The groups $X_1$ and $X_2$ are preferably each bonded to the benzene ring in the ortho-position to the —COR or —CONH group.

When $R_1$ is an alkyl group, it is in particular an alkyl group with 2–4 C atoms and more especially the ethyl or isopropyl group.

If $R_1$ is a cycloalkyl group, it is, for example, the cyclopentyl group and especially the cyclohexyl group.

Alkyl groups $Q_1$, $Q_2$ and/or $Q_3$ are preferably straight-chain and have 1–6 and especially 1–4 C atoms.

Particulary preferred compounds of the formula I, and the corresponding cyclised imide derivatives, are those in which the two R are each —OH, $X_1$ and $X_2$ are each a group

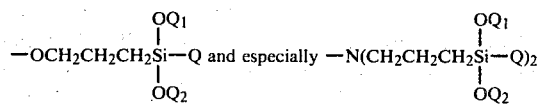

bonded in the ortho-position to the —COR or —CONH group, Q is methyl or alkoxy with 1–4 C atoms and $Q_1$ and $Q_2$ are each alkyl with 1–4 C atoms.

Radicals represented by $Z_1$ in accordance with the definition given may be unsubstituted or substituted, for example by halogen atoms, for instance fluorine, chlorine or bromine, or by alkyl or alkoxy groups, each with 1–4 carbon atoms.

In formula II, the individual symbols m, n, $Z_1$ and $Z_2$ may have different meanings.

Suitable aliphatic radicals $Z_1$ are in particular straight-chain or branched alkylene groups with 2–12 carbon atoms, especially unsubstituted alkylene groups with 2–10 carbon atoms. The alkylene chain may also be interrupted by hetero-atoms, for example O, S or N atoms.

If $Z_1$ is a cycloaliphatic radical it may be, for example, the 1,3- or 1,4-cyclohexylene, 1,4-bis-(methylene)-cyclohexene or dicyclohexylmethane group, whilst suitable araliphatic radicals $Z_1$ are especially 1,3-, 1,4- or 2,4-bis-alkylenebenzene, 4,4′-bis-alkylenediphenyl and 4,4′-bis-alkylene-diphenyl-ether radicals.

If $Z_1$ is a carbocyclic-aromatic radical, it is preferably a monocyclic, fused polycyclic or non-fused bicyclic aromatic radical, and in the latter case the aromatic nuclei may be bonded to one another by a bridge member.

Examples of suitable bridge members are:

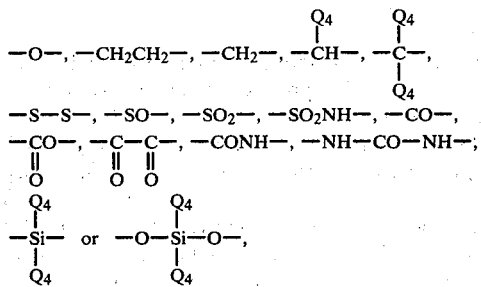

in which $Q_4$ is an alkyl group with 1–6, preferably 1–4, carbon atoms or a phenyl group.

Non-fused bicyclic aromatic radicals $Z_1$ may also be bonded to one another by two bridge members, such as two —SO$_2$— groups.

If $Z_1$ is a heterocyclic-aromatic radical, it is in particular a heterocyclic-aromatic 5-membered or 6-membered ring containing O, N and/or S.

If $Z_2$ is an aliphatic radical, it is preferably an unsubstituted, straight-chain or branched saturated alkylene group with 1–12 carbon atoms, especially an unsubstituted alkylene group with 2–10 carbon atoms.

Cycloaliphatic radicals $Z_2$ are especially 5-membered or 6-membered cycloalkylene groups.

If $Z_2$ is a carbocyclic-aromatic radical, the latter preferably contains at least one 6-membered ring; in particular, such radicals are monocyclic radicals, fused polycyclic radicals, or polycyclic radicals with several cyclic, fused or non-fused, systems, which may be bonded to one another directly or by bridge members. Suitable bridge members are those mentioned above in discussing $Z_1$.

If $Z_2$ is a heterocyclic-aromatic radical, it is in particular a 5-membered or 6-membered heterocyclic-aromatic ring system which contains O, N and/or S, and may be may not be benzo-fused.

Carbocyclic-aromatic or heterocyclic-aromatic radicals $Z_2$ may also be substituted, for example by nitro groups, alkyl groups with 1–4 carbon atoms, halogen atoms, especially chlorine, silyl groups, sulphonic acid groups or sulphamoyl groups.

Preferably, the individual radicals $Z_1$ are, independently of one another, an unsubstituted alkylene group with 2–10 carbon atoms or a monocyclic, or non-fused bicyclic, aromatic radical which is unsubstituted or substituted by halogen, or by alkyl or alkoxy groups, each with 1–4 carbon atoms (the aromatic nuclei, in a non-fused bicyclic aromatic radical, being bonded to one another directly or via a —O—, —CH$_2$— or —SO$_2$— bridge member), or an unsubstituted monocyclic araliphatic radical.

The individual radicals $Z_2$ are preferably, independently of one another, an unsubstituted alkylene group with 2–10 carbon atoms or an unsubstituted monocyclic, fused polycyclic or non-fused bicylic aromatic radical, (the aromatic nuclei, in a non-fused bicyclic radical, being bonded to one another via a —O—, —SO$_2$—or —CO— bridge member).

Preferred compounds of the formula I, and the corresponding cyclised imide derivatives, are those in which a is an integer from 1 to 10, the radicals $Z_1$ are each a 1,3- or 1,4-phenylene group, or a 4,4′-diphenylmethane, 4,4′-diphenyl-ether or 4,4′-diphenylsulphone radical and the radicals $Z_2$ are each a 1,3—or 1,4-phenylene group or unsubstituted alkylene with 4–10 C atoms, if m and n are 1, or each a benzenetriyl group if m is 1 and n is 2, or each a benzenetetrayl group or the benzophenone ring system if m and n are each 2.

Very particularly preferred compounds of the formula 1 and the corresponding cyclised imide derivatives are those in which $X_1$, $X_2$ and R have the above-mentioned preferred meanings, a is an integer from 1 to 10 and either.

m and n are each 1, $Z_1$ is a 1,3- or 1,4-phenylene group or a 4,4′-diphenylmethane or 4,4′-diphenyl-ether radical and $Z_2$ is a 1,3-phenylene or 1,4-phenylene group, but only one of $Z_1$ and $Z_2$ is a 1,4-phenylene group, or m is 1 and n is 2, $Z_1$ is a 1,3- or 1,4-phenylene group or a 4,4′-diphenylmethane or 4,4′-diphenyl-ether radical and $Z_2$ is a benzenetriyl group, or m and n are each 2, $Z_1$ is a 1,3- or 1,4-phenylene group or a 4,4′-diphenylmethane or 4,4′-diphenyl-ether radical and $Z_2$ is a benzenetetrayl group or the benzophenone ring system.

The starting compounds of the formula III may be obtained by a method wherein a compound of the formula V

in which X′ is a

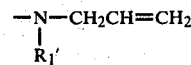

or —O—CH$_2$CH=CH$_2$ group, $R_1'$ is alkyl with 2–7 C atoms, cycloalkyl with 5–7 C atoms, benzyl or allyl and $R_2'$ and $R_3'$ independently of one another are alkoxy with 1–12 C atoms or phenoxy, or $R_2'$ and $R_3'$ together are —O—, is reacted with an at least stoichiometric amount of a compound of the formula VI

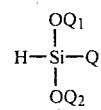 (VI)

in which Q, $Q_1$ and $Q_2$ are defined as under formula I, after which a resulting compound in which $R_2'$ and $R_3'$ together are —O— may or may not be converted to the corresponding free acid.

The silanes of the formula VI are known. Starting compounds of the formula V, in which X' is a diallylamino group, may be prepared by reacting suitable aminophthalic acid derivatives, such as the free acids or the corresponding alkali metal salts, for example the disodium salt or dipotassium salt, with an alkyl halide, especially allyl bromide or allyl chloride, and converting the resulting N,N-bis-allylaminophthalic acid into a compound of the formula V, for example of cyclising to give the anhydride or by esterifying with corresponding alcohols.

Compounds of the formula V, in which X' is an allyloxy group, may be obtained by reacting corresponding hydroxyphthalic anhydrides or hydroxyphthalic acid esters with allyl halides, above all allyl bromide or allyl chloride, in the presence of a base, for example an alkali metal carbonate, e.g. potassium carbonate.

Finally, compounds of the formula V, in which X' is a

group and $R_1''$ is alkyl with 2–7 C atoms, cycloalkyl with 5–7 C atoms or benzyl, can be prepared by reacting a compound of the formula VII

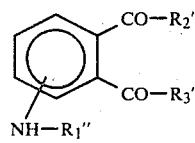 (VII)

in which $R_1''$, $R_2'$ and $R_3'$ are as defined above, with an allyl halide, especially allyl bromide or allyl chloride, preferably in the presence of a base, for example an alkali metal carbonate or alkali metal hydroxide, e.g. potassium carbonate, potassium hydroxide or sodium hydroxide.

The above reactions with allyl halides are advantageously carried out in a polar medium, especially in an aqueous medium, at temperatures between about 0° and 100° C.

The reaction of the compounds of the formula V with the silanes of the formula VI is advantageously carried out in an anhydrous organic medium and in the presence of a catalyst. Examples of suitable catalysts are organic peroxides, such as tert.-butyl hydroperoxide, di-tert.-butyl peroxide, benzoyl peroxide, diacyl peroxides and cumene hydroperoxide, or platinum and palladium catalysts, for example platinum/charcoal catalysts or $PtCl_6H_2$ catalysts.

Examples of suitable inert organic solvents are aromatic hydrocarbons, for example benzene, toluene and xylenes, cyclic ethers, for example tetrahydrofuran, tetrahydropyran and dioxane, or ethylene glycol monoalkyl ethers and dialkyl ethers with 1–4 C atoms in each alkyl part, such as ethylene glycol monomethyl ether, monoethyl ether, diethyl ether and di-n-butyl ether. Aromatic hydrocarbons are preferred.

The reaction is advantageously carried out under a protective gas, for example nitrogen or argon.

The reaction temperatures are in general approximately between 80° and 150° C.; reaction temperatures between about 90° and 120° C. are preferred.

If desired, the resulting anhydrides of the formula III can be hydrolysed to the free acids by methods known per se.

The compounds of the formula IV which can be employed in the process according to the invention are known or can be prepared by methods known per se.

The following may be mentioned as examples of monomeric diamines of the formula IV: o-, m- and p-phenylenediamine, diaminotoluenes, for example 2,4-diaminotoluene, 1,4-diamino-2-methoxybenzene, 2,5-diaminoxylene, 1,3-diamino-4-chlorobenzene, 4,4,'-diaminodiphenylmethane, 4,4'-diaminodiphenyl-ether, 4,4'-diaminodiphenyl-thioether, 4,4'-diaminodiphenyl-sulphone, 2,2'-diaminobenzophenone, 4,4'-diaminodiphenylurea, 1,8- or 1,5-diaminonaphthalene, 2,6-diaminopyridine, 2,4-diaminopyrimidine, 2,4-diamino-s-triazine, di-, tri-, tetra-, hexa-, hepta-, octa-, deca- and dodeca-methylenediamine, 2,2-dimethylpropylenediamine, 2,5-dimethylhexamethylenediamine, 4,4-dimethylheptamethylenediamine, 3-methylheptamethylenediamine, methylenediamine, 3-methoxyhexamethylenediamine, 2,11-diaminododecane, 2,2,4- and 2,4,4-trimethylhexamethylenediamine, 1,2-bis-(3-aminopropoxy)-ethane, N,N'-dimethylethylenediamine, N,N'-dimethyl-1,6-diaminohexane as well as the diamines of the formulae $H_2N(CH_2)_3O(CH_2)_2O(CH_2)_3NH_2$ and $H_2N(CH_2)_3S(CH_2)_3NH_2$, 1,4-diaminocyclohexane, 1,4-bis-(2-methyl-4-aminopentyl)-benzene and 1,3- and 1,4-bis-(aminomethyl)-benzene.

Mixtures of different monomeric diamines of the formula IV can also be used.

Compounds of the formula IV, in which Y is a structural element of the formula II and a is an integer from 2 to 15 may be obtained by a method known per se, wherein a dicarboxylic, tricarboxylic or tetracarboxylic acid derivative of the formula VIII

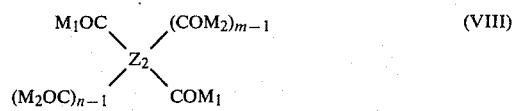 (VIII)

in which m, n and $Z_2$ are as defined under formula II and $M_1$ is a chlorine atom, a hydroxyl group, an alkoxy group with 1–12 C atoms or a phenoxy group or $M_1$, if m and/or n are 2, together with one $M_2$ forms the —O— group, the groups —$COM_1$ and $COM_2$ are bonded to different carbon atoms, and if $Z_2$ is a cyclic radical and m and/or n are 2, the —$COM_1$ group or groups are in the ortho-position to a —$COM_2$ group, is condensed with an excess of a diamine of the formula IX

  $H_2N-Z_1-NH_2$ (IX)

in which $Z_1$ is as defined under formula II, after which the product obtained may or may not be cyclised. In this reaction, mixtures of different compounds of the formula VIII and diamines of the formula IX may also be used.

If $M_1$ is an alkoxy group with 1-12 carbon atoms, preferably 1-4 C atoms, suitable groups are, for example, those mentioned above when discussing R, $R_2$ and $R_3$.

The compounds of the formulae VIII and IX are known per se. Diamines $H_2N$—$Z_1$—$NH_2$ which may be used are, for example, compounds of the abovementioned type. Examples of suitable dicarboxylic, tricarboxylic and tetracarboxylic acid derivatives of the formula VIII are malonic acid, dimethylmalonic acid, succinic acid, glutaric acid, adipic acid, suberic acid, sebacic acid, dodecanedicarboxylic acid, 1,3-cyclopentanedicarboxylic acid, hexahydroisophthalic acid, hexahydroterephthalic acid, terephthalic acid, isophthalic acid, 4,4'-dicarboxydiphenylethane, naphthalene-2,6-dicarboxylic acid, thiophene-2,5-dicarboxylic acid and pyridine-2,3-dicarboxylic acid, as well as the corresponding dichlorides and the diesters which accord with the definition; trimellitic acid 1,2-anhydride chloride (1,3-dioxo-benzo-[c]-oxalane-5-carboxylic acid chloride), trimellitic anhydride as well as the esters which accord with the definition; pyromellitic dianhydride, 3,3'-4,4'-benzophenone-tetracarboxylic acid dianhydride, 2,3,3',4'-benzophenone-tetracarboxylic acid dianhydride, 2,2',3,3'-benzophenone-tetracarboxylic acid dianhydride, 3,3',4,4'-diphenyl-tetracarboxylic acid dianhydride, bis-(2,3-dicarboxyphenyl)-methane dianhydride, bis-(2,5,6-trifluoro-3,4-dicarboxyphenyl)-methane dianhydride, 2,2-bis-(2,3-dicarboxyphenyl)-propane dianhydride, bis-(3,4-dicarboxyphenyl)-ether dianhydride, bis-(3,4-dicarboxyphenyl)-sulphone dianhydride, N,N-(3,4-dicarboxphenyl)-N-methylamine dianhydride, bis-(3,4-dicarboxyphenyl)-diethylsilane dianhydride, 2,3,6,7- and 1,2,5,6-naphthalene-tetracarboxylic acid dianhydride, 2,6-dichloronaphthalene-1,4,5,8-tetracarboxylic acid dianhydride, thiophene-2,3,4,5-tetracarboxylic acid dianhydride, pyrazine-2,3,5,6-tetracarboxylic acid dianhydride and pyridine-2,3,5,6-tetracarboxylic acid dianhydride.

The preferred dicarboxylic acid derivatives are dicarboxylic acid dichlorides.

The condensation of the compounds of the formula III and VIII with the compounds of the formula IV or the diamines $H_2N$—$Z_1$—$NH_2$ is carried out in a manner known per se, advantageously at temperatures from about $-50°$ C. to $+300°$ C. The condensation may be carried out in the melt or, preferably, in an inert organic solvent or a solvent mixture. Preferred temperatures for the condensation in solution are from $-20°$ C. to $+200°$ C., more especially from $-20°$ C. to $+50°$ C.

Examples of organic solvents which may be employed are chlorinated and non-chlorinated aromatic hydrocarbons, for example benzene, toluene, xylenes and chlorobenzene; chlorinated aliphatic hydrocarbons, for example methylene chloride, chloroform, tetrachloroethane and tetrachloroethylene; aliphatic and cycloaliphatic ketones, for example acetone, methyl ethyl ketone, cyclopentanone and cyclohexanone; cyclic ethers, for example tetrahydrofuran, tetrahydropyran and dioxane; cyclic amides, for example N-methyl-2-pyrrolidone, N-acetyl-2-pyrrolidone and N-methyl-$\epsilon$-caprolactam; N,N-dialkylamides of aliphatic monocarboxylic acids with 1-3 carbon atoms in the acid part, for example N,N-dimethylformamide, N,N-dimethylacetamide, N,N-diethylacetamide and N,N-dimethylmethoxyacetamide; ethylene glycol monoalkyl and dialkyl ethers with 1-4 carbon atoms in each alkyl part, for example ethylene glycol monomethyl ether, monoethyl ether, monoisopropyl ether and mono-n-butyl ether and ethylene glycol dimethyl ether and diethyl ether; alkyl esters of aliphatic monocarboxylic acids with a total of 2-6 carbon atoms, for example methyl, ethyl and n-butyl formate or acetate; hexamethylphosphorotriamide (hexametapol); N,N,N',N'-tetramethylurea; tetrahydrothiophene dioxide (sulpholane); dialkylsulphoxides, for example dimethylsulphoxide and diethylsulphoxide; phenol and cresols.

Mixtures of these types of solvents may also be used.

Preferred solvents are N,N-dialkylamides of aliphatic monocarboxylic acids with 1-3 carbon atoms in the acid part, especially N,N-dimethylacetamide, and cyclic amides, for example N-methylpyrrolidone.

The hydrochloric acid formed during the condensation or polycondensation of a compound of the formula VIII, in which $M_1$ is chlorine, with a diamine $H_2N$—$Z_1$—$NH_2$, can be removed by neutralisation with basic compounds, for example calcium hydroxide or triethylamine, or by reaction with an epoxide compound, for example ethylene oxide or propylene oxide, and by washing out with a suitable solvent, for example water.

The condensation reactions are advantageously carried out with exclusion of moisture, for example in an inert gas atmosphere, for instance nitrogen.

The compounds of the formula III are reacted with the compounds of the formula IV in a molar ratio of at least 2:1. Where the compound of the formula IV is a monomeric diamine, the latter is advantageously used in the stoichiometric amount or slightly less than this amount. For the reaction with oligomers or polymers, possessing amino end groups, of the formula IV, the reactants are preferably employed in the stoichiometric amount.

During the optional cyclisation of the compounds of the formula I or IV obtained after condensation, imide formation occurs. The cyclisation is carried out chemically or thermally, by methods known per se.

Chemical cyclisation is advantageously effected by treatment with a dehydrating agent, used by itself or mixed with a tertiary amine. Examples of suitable dehydrating agents are acetic anhydride, propionic anhydride and dicyclohexylcarbodiimide, or mixtures of acetic anhydride and triethylamine.

Thermal cyclisation is effected by heating to temperatures of about $50°$–$250°$ C., preferably about $100°$–$150°$ C., in the presence or absence of an inert organic solvent and/or an azeotropic entraining agent, for example xylenes or toluene. At temperatures above $150°$ C., at least partial crosslinking also generally occurs.

The compounds according to the invention, of the formula I, and the corresponding cyclised derivatives can also be crosslinked chemically or thermally, in accordance with methods known per se, to give polymers.

The compounds of the formula I are valuable adhesion promoters, especially between inorganic solids and organic resins, and may be used for a large number of applications in the adhesives industry and in the lacquer-using and plastics-processing industries.

The following are examples of some fields of use: improving the adhesion of special sealants, for example polysulphides, polyurethanes and polyacrylates, to various substrates, for example glass, aluminium and ceramics; encapsulating mineral fillers so as to improve the mechanical properties of the products prepared therewith, for example in the case of sand-filled masks and cores used in the foundry industry, mineral-filled cable mixtures or other mineral-filled plastics, for example filled thermosetting resins, for instance quartz-filled epoxide resins and filled unsaturated polyesters, filled thermoplastics, for instance polyamide-6,6 and polyethylene terephthalate, and filled elastomers, for instance natural rubber and synthetic rubber; and incorporation in adhesives, adhesive compositions and lacquers, for example adhesive compositions containing epoxide resins, and lacquers based on epoxides, polyacrylates, polyurethanes and vinyl chloride copolymers. However, the compounds mentioned are especially suitable for the manufacture of reinforced plastics, especially glass fibre-reinforced plastics, in particular composite materials, for instance laminates, in order to improve the adhesion between the substrate or matrix and the plastic applied thereto. The substrate per se may be in any desired form, for example in the form of fibres, fabrics or nonwovens, and preferably consists of glass or of mineral materials, for example quartz, mineral wool, asbestos, mica or metal fibres and foils. Examples of suitable plastics for the manufacture of such laminates are acrylates and polyester, epoxide, silicon, melamine, phenolic and furan resins, and also polyamides, polyamidoacids and polyimides, but especially polymers crosslinkable via C=C double bonds, for instance unsaturated polyesters, homopolymers and copolymers containing maleimidyl and nadicimidyl groups, their precursors or their mixtures with other polymers.

Relative to comparable composite materials which have been manufactured using known silicon-containing adhesion promoters, especially those of the type mentioned at the outset, glass fibre-reinforced composite materials manufactured using the adhesion promoters according to the invention, of the formula I, are distinguished especially by improved resistance to thermal oxidation, improved dielectric properties after exposure to moisture, and/or lower water absorption. The compounds of the formula I are also distinguished by good wetting of the substrates.

The adhesion promoters according to the invention are advantageously applied in the form of solutions in suitable organic solvents, for example N,N-dimethylformamide, N,N-dimethylacetamide, N-methyl-2-pyrrolidone, acetone, methyl ethyl ketone, tetrahydrofuran and dioxane.

PREPARATION EXAMPLES

Example 1

In a sulphonation flask, 4.00 g (0.02 mol) of 4,4'-diaminodiphenyl ether are dissolved in 90 ml of anhydrous N,N-dimethylacetamide (DMA) under a nitrogen atmosphere, and 3.27 g (0.015 mol) of pyromellitic dianhydride are added in portions, at 0° C. The reaction mixture is stirred for one hour at 20°-25° C. 6.56 g (0.01 mol) of 3-N,N-bis-[3-(tri-n-propoxy)-silyl-propyl]-aminophthalic anhydride are then added at 0° C. and the reaction mixture is stirred for a further hour at 20°-25° C. The resulting polyamidoacid solution may be used as an adhesion promoter for finishing glass fibre fabrics which can be used for the manufacture of glass fibre-reinforced laminates.

3-N,N-bis-[3-(Tri-n-propoxy)-silyl-propyl]-aminophthalic anhydride, used in the above example, may be prepared as follows:

In a sulphonation flask, 50 g (0.205 mol) of 3-N,N-diallylamino-phthalic anhydride are dissolved in 250 ml of anhydrous toluene under a nitrogen atmosphere, and heated to 115° C. At this temperature, a solution of 115 g (0.55 mol) of tri-n-propoxysilane and 2 ml of an 0.02 molar solution of hexachloroplatinic acid ($H_2PtCl_6.6H_2O$) in propanol, all in 50 ml of anhydrous toluene, is added dropwise in the course of 20 minutes, with stirring. The reaction mixture is then stirred for a further 10 hours at 110° C. The solvent and excess tri-n-propoxysilane are removed in vacuo. 111 g (83% of theory) of 3-N,N-bis-[3-(tri-n-propoxy)-silylpropyl]-aminophthalic anhydride are obtained in the form of a reddish oil.

Analysis for $C_{32}H_{57}BO_9Si_2$ (molecular weight 656): calculated: C, 58.59%; H, 8.76%; N, 2.14%; Si, 8.56%. found: C, 59.0%; H, 8.4%; N, 2.5%; Si, 8.0%.

3-N,N-Diallylamino-phthalic anhydride, used as the starting material, may be prepared as follows: 225 g (1.0 mol) of disodium 3-aminophthalate and 138 g (1.0 mol) of potassium carbonate are dissolved in 400 ml of water. 317.2 g (2.6 mols) of allyl bromide are added to the solution at about 25° C. and the reaction mixture is stirred for 4 hours at 30°-35° C. The diallylaminophthalic acid is precipitated by adding 200 ml of 35% aqueous hydrochloric acid. The product is filtered off at 10° C., washed with 100 ml of water and dried. 261 g (1 mol) of the resulting 3-N,N-diallylaminophthalic acid are heated to 150°-155° C. A melt is formed; this is stirred for 2 hours at about 150° C. whilst passing a stream of nitrogen over it, and is then allowed to cool to 50° C. 750 ml of toluene and 750 ml of n-hexane are then added and the crude product is recrystallised from this mixture. 237 g of 3-N,N-diallylaminophthalic anhydride are obtained; melting point 94°-95° C.

EXAMPLE 2

In a sulphonation flask, 3.24 g (0.03 mol) of m-phenylenediamine are dissolved in 110 ml of anhydrous DMA under a nitrogen atmosphere, and cooled to between −15° C. and −20° C. 5.07 g (0.025 mol) of isophthalic acid dichloride are added dropwise to this solution, with stirring, under conditions such that the temperature does not rise above −15° C. The reaction mixture is then stirred for one hour at 20°-25° C. Thereafter, a solution of 5.06 g (0.05 mol) of triethylamine in 10 ml of DMA is added dropwise at −15° C. After stirring for a further hour at 20°-25° C., the reaction solution is cooled to 0° C., 9.08 g (0.01 mol) of 3-N,N-bis-[3-(tri-n-hexyloxy)-silyl-propyl]-aminophthalic anhydride are added and the solution is stirred for a further hour at 20°-25° C. After filtering off the triethylamine hydrochloride which has precipitated, the 10% polyamide solution obtained is used for finishing glass fibre fabrics.

The 3-N,N-bis-[3-(tri-n-hexyloxy)-silyl-propyl]-aminophthalic anhydride used as the starting material is prepared by a method analogous to that described in Example 1.

EXAMPLE 3

Using the procedure described in Example 2, 4.96 g (0.025 mol) of 4,4'-diaminodiphenylmethane, 4.0 g (0.02 mol) of trimellitic anhydride chloride, 2.02 g (0.02 mol) of triethylamine and 6.56 g (0.01 mol) of 3-N,N-bis-[3-

(tri-n-propoxy)-silyl-propyl]-aminophthalic anhydride are reacted in 150 ml of anhydrous DMA. The resulting 10% polyamide-amidoacid solution can be used for finishing glass fibre fabrics.

EXAMPLE 4

In a sulphonation flask, 1.98 g (0.01 mol) of 4,4'-diaminodiphenylmethane (DDM) are dissolved in 142 ml of anhydrous N,N'-dimethylformamide (DMF) under a nitrogen atmosphere and 13.1 g (0.02 mol) of 4-N,N'-bis-[3-(tri-n-propoxy)-silyl-propyl]-aminophthalic anhydride are added dropwise at 0° C. The mixture is stirred for a further hour, at 20° to 25° C. The resulting amidoacid solution can be used for finishing glass fibres.

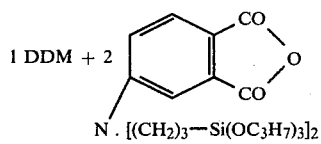

EXAMPLE 5

In a sulphonation flask, 4.46 g (0.018 mol) of 4,4'-diaminodiphenylsulphone are dissolved in 80 ml of anhydrous DMA under a nitrogen atmosphere, and 5.14 g (0.016 mol) of 3,3'-4,4'-benzophenone-tetracarboxylic acid dianhydride are added in portions at 0° C. The reaction mixture is stirred for one hour at 20° to 25° C. A solution of 1.46 g (0.004 mol) of 3-(γ-(methyl-di-n-propoxysilyl)-propoxy-phthalic anhydride in 25 ml of DMA is then added at 0° C. and the reaction mixture is stirred for a further hour, at 20° to 25° C. The resulting polyamidoacid solution may be used as an adhesion promoter for finishing glass fibre fabrics which can be used for the manufacture of glass fibre-reinforced laminates.

EXAMPLE 6

In a sulphonation flask, 4.32 g (0.04 mol) of 1,3-phenylenediamine are dissolved in 100 ml of anhydrous N,N'-dimethylacetamide under a nitrogen atmosphere, and cooled to between $-15°$ and $-20°$ C. 7.17 g (0.03 mol) of sebacic acid dichloride are added dropwise to this solution, with stirring, under conditions such that the temperature does not exceed $-15°$ C. The reaction mixture is then stirred for one hour at 20° to 25° C. 3.04 g (0.03 mol) of triethylamine are then added dropwise at $-15°$ C. After stirring for a further hour at 20° to 25° C., the reaction solution is cooled to 0° C. and a solution of 8.43 g (0.02 mol) of 4-[N-butyl-N'-(methyl-di-n-propoxy)-silyl-propyl]-aminophthalic anhydride (see Example 9) in 50 ml of N,N'-dimethylacetamide is added dropwise. The reaction solution is stirred for a further hour at 20° to 25° C. After filtering off the triethylamine hydrochloride which has precipitated, the polyamidoacid solution obtained is used for finishing glass fibre fabrics.

EXAMPLE 7

In a sulphonation flask, 18.20 g (0.0908 mol) of N,N'-4,4-diaminodiphenyl ether (DDE) are dissolved in 590 ml of anhydrous N,N'-dimethylacetamide (=DMA) under a nitrogen atmosphere, and the solution is cooled to 0°-5° C. 14.87 g (0.068 mol) of pyromellitic acid dianhydride (PMSDA) are added in portions, with stirring. After stirring for one hour at 0°-5° C., 29.81 g (0.045 mol) of 3-N,N'-bis-[3-(tri-n-propoxy)-silyl-propyl]-amino-phthalic anhydride are added dropwise. The mixture is then stirred for a further hour, at 20°-25° C. The resulting polyamidoacid solution can be used for finishing glass fibres.

EXAMPLE 8

In a sulphonation flask, 3.24 g (0.03 mol) of 1,3-phenylenediamine are dissolved in 110 ml of anhydrous N,N'-dimethylacetamide under a nitrogen atmosphere, and the solution is cooled to between $-15°$ C. and $-20°$ C. 5.07 g (0.025 mol) of isophthalic acid dichloride are added in portions, with stirring, under conditions such that the temperature does not exceed $-15°$ C. The mixture is then stirred for 1 hour at 20°-25° C., after which a solution of 5.06 g (0.05 mol) of triethylamine in 10 ml of N,N-dimethylacetamide is added dropwise at $-15°$ C. After stirring for 1 hour at 20°-25° C., the reaction solution is cooled to 0° C. and 9.08 g (0.01 mol) of 3-N,N'-bis-[3-(tri-n-hexoxy)-silyl-propyl]-aminophthalic anhydride are added dropwise. Stirring is then continued for 1 hour at 20°-25° C., after which the triethylamine hydrochloride which has precipitated during the reaction is filtered off. The resulting polyamidoacid solution can be used for finishing glass fibres.

USE EXAMPLES (a) Impregnation of Glass Fibre Fabrics

A glass fibre fabric made from so-called E-glass, with satin weave and weighing 280 g/m², is first thermally desized to about 0.1% by weight residual size content and is then impregnated with 2% solutions of the adhesion promoters listed below. The adhesion promoter solutions are applied by immersion, with an impregnation speed of 0.5 m/minute, and the impregnated material is then dried for 20 minutes at 180° C. in a circulating air oven.

The prepegs obtained contain from 0.09 to 0.15% by weight, based on glass, of adhesion promoter.

The following are used as adhesion promoters (finishes):

(1) No adhesion promoter
(2) Vinyl-tris-(2-methoxyethoxy)-silane ("Silan A 172" from Messrs. Union Carbide); 2% solution in N,N-dimethylformamide (DMF)
(3) γ-Aminopropyl-triethoxysilane ("Silan A 1100" from Messrs. Union Carbide); 5% solution in N,N-dimethylformamide.
(4) Chromium chloride methacrylate complex ("Volan-A" from Messrs. DuPont); 2% solution in DMF
(5) Polyamidoacid solution according to Preparation Example 1, diluted to 2% by weight with DMF
(6) Polyamide solution according to Preparation Example 2, diluted to 2% by weight with DMF
(7) Polyamidoacid solution according to Preparation Example 3, diluted to 2% by weight with DMF
(8) Polyamidoacid solution according to Preparation Example 5, diluted to 2% by weight with DMF
(9) Polyamidoacid solution according to Preparation Example 4, diluted to 2% by weight with DMF
(10) Polyamidoacid solution according to Preparation Example 8, diluted to 2% by weight with DMF.

(b) Production of Copper-Covered Laminate Sheets Based on a Bis-Maleimide 1.0 mol of N,N'-4,4'-diphenylmethane-bis-maleimide is dissolved in 500 g of furfuryl alcohol at 100° C. and the solution is cooled to 25° C. 0.4 mol of 4,4'-diaminodiphenylmethane is dissolved in 200 g of methylglycol at 25° C. The two solutions are combined and mixed thoroughly. The glass fibre fabrics finished in accordance with section (a) are impregnated with this mixed solution by the immersion process at 25° C. and are then dried in a circulating air oven for 18 minutes at 180° C.; the resulting prepegs contain 39% by weight of resin. 10 layers of the impregnated fabric are then pressed hot between two 35 microns thick copper foils which have been pretreated by electrolytic surface coating with brass. The press is first kept under light contact pressure for 2 to 3 minutes; the pressure is then raised to 40 kp/cm² and the assembly is pressed for one hour at 180° C. The test specimens are then taken out of the press and post-cured for a further 6 hours in an oven at 240° C.; the resulting laminate sheets contain 35% by weight of resin.

(c) Production of Copper-Covered Laminate Sheets Based on an Epoxide Resin (Triglycidyl ether based on dimethylhydantoin of the formula

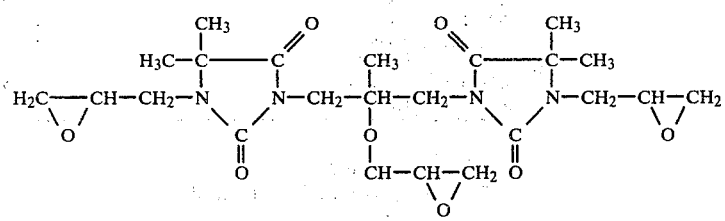

curing agent: cresyl novolac)

100 g of the above triglycidyl compound are dissolved in 25 g of acetone at 60° C. 66 g of the curing agent are dissolved in 30 g of acetone at 60° C. The two solutions are cooled to 25° C., combined with one another, with addition of 0.25 g of 2-phenylimidazole, and mixed thoroughly.

The glass fabrics finished in accordance with section (a) are impregnated by the immersion method at 25° C. and then dried for 11 minutes at 150° C. in a circulating air oven. The pressing procedure is then carried out as described under (b), followed by the post-curing (10 hours at 200° C.).

(d) Production of Copper-Covered Laminate Sheets Based on an Epoxide Resin

[Cycloaliphatic diepoxide (5 epoxy equivalents/kg) of the formula

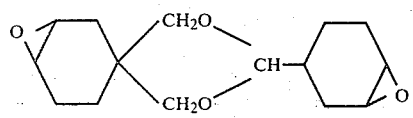

curing agent: boron trifluoride/amine complex]

125 g of the above diepoxide and 2 g of the curing agent are dissolved at 50° C. and the solution is then cooled to 25° C. The finished glass fabrics are impregnated by the immersion method at 25° C. and are then dried for 6 minutes at 150° C. in a circulating air oven. Thereafter the material is pressed for one hour at 160° C. analogously to section (b). After the pressing procedure, the laminates are post-cured for 3 hours in an oven at 180° C.

(e) Production of Copper-Covered Laminate Sheets Based on an Epoxide Resin (80% strength solution of a diglycidyl ether of tetrabromobisphenol A in methyl ethyl ketone [2 epoxy equivalents/kg]; curing agent: 10% solution of dicyandiamide in ethylglycol)

125 g of the above diglycidyl ether, 30 g of curing agent, 0.2 g of benzyldimethylamine, 10 g of methylglycol and 10 g of acetone are combined at 25° C., and mixed.

The glass fabrics finished in accordance with section (a) are impregnated by the immersion method at 25° C., then dried for 10 minutes at 150° C. in a circulating air oven, and pressed for one hour at 180° C., analogously to the procedure in section (b) (without post-curing).

Properties of the Resulting Copper-Covered Laminate Sheets According to Examples I(b), (c), (d) and (e).

Flexural strength in N/mm² according to ISO/R 178
  (a) Initial value
  (b) After 10 days' aging at 270° C.
Water absorption
  In % by weight at 23° C. after 24 hours. The measurements are carried out on flexural test specimens according to VSM Standard Specification 77,103.
Dielectric loss factor tg δ/50 c/s according to DIN 53,483
  (a) Initial value measured at 23° C.
  (b) After 6 hours' storage in boiling water
Dielectric constant $\epsilon_r$/50 c/s according to DIN 53,483
  (a) Initial value measured at 23° C.
  (b) After 6 hours' storage in boiling water
ISO/R = International Standards Organisation/Recommendations
VSM = Verein Schweizerischer Maschinenindustrieller
DIN = Deutsche Industrie-Norm The results are summarised in Tables I to IV which follow. The numbering of the experimental products and of the test specimens is the same as under (a).

TABLE I (Test values of the laminate sheets according to Example Ib)

| | Adhesion promoter Product No. | | | | | | | | | |
|---|---|---|---|---|---|---|---|---|---|---|
| | 1 | 2 | 3 | 4 | 5 | 6 | 7 | 8 | 9 | 10 |
| Flexural strength, N/mm², initial value | 422.3 | 401 | 586.7 | 553.2 | 569.4 | 603.6 | 455.4 | 436.4 | 349.1 | 339.5 |
| After 10 days' aging at 270° C. | 282.4 | 108.8 | 162.8 | 220.3 | 296.1 | 458.2 | 325.5 | 318.4 | 207.2 | 307.6 |
| Water absorption in % by weight after 24 hours at 23° C. | 0.54 | 0.28 | 0.29 | 0.23 | 0.13 | 0.08 | 0.18 | 0.25 | 0.22 | 0.17 |
| Dielectric loss factor, δ/50 c/s, initial value | 1.08 | 1.15 | 2.71 | 0.86 | 0.31 | 0.29 | 0.28 | 0.26 | 0.27 | 0.24 |
| After 6 hours' storage in boiling water | 6.57 | 2.81 | 4.22 | 1.93 | 1.40 | 0.96 | 0.49 | 0.39 | 0.40 | 0.50 |
| Dielectric constant $\epsilon_r$/50 c/s, initial value | 5.1 | 5.4 | 5.1 | 6.6 | 5.2 | 5.2 | 5.0 | 5.1 | 5.0 | 5.2 |
| After 6 hours' storage in boiling water | 6.9 | 5.8 | 5.5 | 7.9 | 5.7 | 5.5 | 5.2 | 5.4 | 5.2 | 5.5 |

TABLE II (Test data of the laminate sheets according to Example Ic)

| | Adhesion promoter Product No. | | |
|---|---|---|---|
| | 1 | 4 | 9 |
| Flexural strength, N/mm², initial value | 342.5 | 523.4 | 318.8 |
| After 10 day's aging at 220° C. | 358.0 | 469.1 | 314.8 |
| After 6 hours' storage in boiling water | 328.5 | 440.7 | 365.3 |
| Change in % | −4.1 | −15.8 | +14.6 |
| Dielectric loss factor δ/50 c/s, initial value | 0.40 | 0.46 | 0.45 |
| After 6 hours' storage in boiling water | 3.44 | 2.01 | 1.14 |
| Dielectric constant $\epsilon_r$/50 c/s, initial value | 5.3 | 4.9 | 4.8 |
| After 6 hours' storage in boiling water | 6.4 | 5.8 | 5.1 |

TABLE III (Test data of the laminate sheets according to Example Id)

| | Adhesion promotor Product No. | | | |
|---|---|---|---|---|
| | 1 | 4 | 8 | 9 |
| Flexural strength, N/mm², initial value | 329.5 | 421.4 | 361.5 | 328.3 |
| After 20 days' aging at 220° C. | 295.3 | 397.7 | 349.6 | 299.7 |
| After 6 hours' storage in boiling water | | | | |
| Change in % | | | | |
| Dielectric loss factor δ/50 c/s, initial value | 0.35 | 0.37 | 0.30 | 0.30 |
| After 6 hours' storage in boiling water | 1.64 | 1.64 | 1.27 | 1.25 |
| Dielectric constant $\epsilon_r$/50 c/s, initial value | 4.3 | 4.2 | 4.0 | 4.1 |
| After 6 hours' storage in boiling water | 4.5 | 4.5 | 4.3 | 4.4 |

TABLE IV (Test data of the laminate sheets according to Example Ie)

| | Adhesion promoter Product No. | | |
|---|---|---|---|
| | 1 | 4 | 9 |
| Flexural strength, N/mm², initial value | 373.5 | 530.9 | 354.3 |
| After 6 days' aging at 180° C. | 321.4 | 519.8 | 329.7 |
| After 6 hours' storage in boiling water | 222.8 | 475.4 | 375.7 |
| Change in % | −40.4 | −10.5 | +6.0 |
| Dielectric loss factor δ/50 c/s, initial value | 0.38 | 0.45 | 0.34 |
| After 6 hours' storage in boiling water | 39.10 | 4.05 | 3.62 |
| Dielectric constant $\epsilon_r$/50 c/s, initial value | 5.0 | 5.0 | 4.9 |
| After 6 hours' storage in boiling water | 16.3 | 5.7 | 5.5 |

What is claimed is:

1. A compound of the formula I

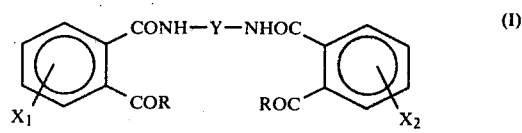

and the corresponding cyclised imide derivatives, in which $X_1$ and $X_2$ independently of one another are a group

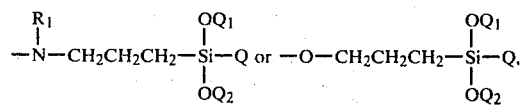

the two R independently of one another are —OH, alkoxy with 1–12 C atoms or phenoxy, $R_1$ is alkyl with 2–7 C atoms, cycloalkyl with 5–7 C atoms, benzyl or

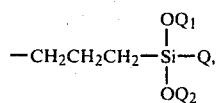

Q is methyl, phenyl or —OQ$_3$, Q$_1$ Q$_2$ and Q$_3$ independently of one another are alkyl with 1–6 C atoms or phenyl and Y is a structural element of the formula II

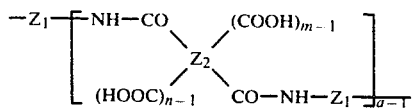

in which a is an integer from 1 to 15, the individual indices m and n independently of one another are 1 to 2, the individual radicals $Z_1$ independently of one another are an aliphatic radical with at least 2 C atoms, or a cycloaliphatic, araliphatic, carbocyclic-aromatic or heterocyclic-aromatic radical and the individual radicals $Z_2$ independently of one another are an aliphatic radical with at least 2 C atoms, or a cycloaliphatic, carbocyclic-aromatic or heterocyclic-aromatic radical, in which the carboxamide and carboxyl groups are bonded to different C atoms, and carboxyl groups bonded to cyclic radicals $Z_2$ are each in the ortho-position to a carboxamide group.

2. A compound of the formula I according to claim 1, and the corresponding cyclised imide derivative, in which $X_1$ and $X_2$ are each bonded to the benzene ring in the ortho-position to the —COR or —CONH group, and the two R are each —OH.

3. A compound of the formula I according to claim 1, and the corresponding cyclised imide derivative, in which the two R are each —OH, $X_1$ and $X_2$ are each a group

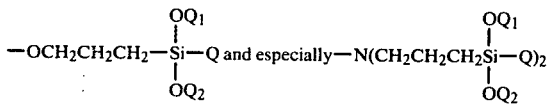

bonded in the ortho-position to the —COR or —CONH group, Q is methyl or alkoxy with 1-4 C atoms and $Q_1$ and $Q_2$ are each alkyl with 1-4 C atoms.

4. A compound of the formula I according to claim 1, and the corresponding cyclised imide derivative, in which the individual radicals $Z_1$ independently of one another are an unsubstituted alkylene group with 2-10 C atoms, an unsubstituted monocyclic araliphatic radical, or a monocyclic, or non-fused bicyclic, aromatic radical which is unsubstituted or substituted by halogen atoms or alkyl or alkoxy groups each with 1-4 C atoms, (the aromatic nuclei, in a non-fused bicyclic aromatic radical being bonded to one another directly or via a —C—, —CH$_2$— or —SO$_2$— bridge member) and the individual radicals $Z_2$ independently of one another are an unsubstituted alkylene group with 2-10 C atoms or an unsubstituted monocyclic, fused polycyclic or non-fused bicyclic aromatic radical, the aromatic nuclei in a non-fused bicyclic aromatic radical being bonded to one another via a —O—, —SO$_2$— or —CO— bridge member.

5. A compound of the formula I according to claim 1, and the corresponding cyclised imide derivatives, in which a is an integer from 1 to 10, the radicals $Z_1$ are each a 1,3- or 1,4-phenylene group, or a 4,4'-diphenylmethane, 4,4'-diphenyl-ether or 4,4'-diphenylsulphone radical and the radicals $Z_2$ are each a 1,3- or 1,4 -phenylene group or unsubstituted alkylene with 4–10 C atoms, if m and n are 1, or each a benzenetriyl group if m is 1 and n is 2, or each a benzenetetrayl group or the benzophenone ring system if m and n are each 2.

6. A compound of the formula I according to claim 1, in which a is an integer from 1 to 10, m and n are 1, $Z_2$ is a 1,3- or 1,4-phenylene group and $Z_1$ is a 1,3- or 1,4-phenylene group or a 4,4'-diphenylmethane or 4,4'-diphenylether radical, but only one of $Z_1$ and $Z_2$ is a 1,4-phenylene group.

7. A compound of the formla I according to claim 1, and the corresponding cyclised imide derivatives, in which a is an integer form 1 to 10, m is 1 and n is 2, $Z_2$ is a benzenetriyl group and $Z_1$ is a 1,3- or 1,4-phenylene group or a 4,4'-diphenylmethane or 4,4'-diphenyl-ether radical.

8. A compound of the formula I according to claim 1, and the corresponding cyclised imide derivatives, in which a is an integer from 1 to 10, m and n are 2, $Z_2$ is a benzenetetrayl group or the benzophenone ring system and $Z_1$ is a 1,3- or 1,4-phenylene group or a 4,4'-diphenylmethane or 4,4'-diphenyl-ether radical.

9. A compound of formula I according to claim 1, wherein Y is

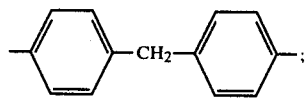

$X_1$ and $X_2$ are N[—CH$_2$CH$_2$CH$_2$Si(OC$_3$H$_7$)$_3$]$_2$; and R is OH.

* * * * *

UNITED STATES PATENT AND TRADEMARK OFFICE
CERTIFICATE OF CORRECTION

PATENT NO. : 4,306,073
DATED : DECEMBER 15, 1981
INVENTOR(S) : ROLAND DARMS ET AL

It is certified that error appears in the above—identified patent and that said Letters Patent is hereby corrected as shown below:

Claim 4, Column 18, Line 1 reads:

"-C-, -CH$_2$- or -SO$_2$- bridge member) and the"

Should read:

-- -O-, -CH$_2$- or -SO$_2$- bridge member) and the --

Signed and Sealed this

Sixteenth Day of March 1982

[SEAL]

Attest:

GERALD J. MOSSINGHOFF

Attesting Officer    Commissioner of Patents and Trademarks